United States Patent [19]
Gold et al.

[11] Patent Number: 4,818,749
[45] Date of Patent: Apr. 4, 1989

[54] CARBOXYALKYL DIPEPTIDES AND MEDICAL USE THEREOF IN TREATING HYPERTENSION AND CONGESTIVE HEART FAILURE

[75] Inventors: Elijah H. Gold; Bernard R. Neustadt, both of West Orange; Elizabeth M. Smith, Verona, all of N.J.

[73] Assignee: Schering Corporation, Kenilworth, N.J.

[21] Appl. No.: 117,008

[22] Filed: Nov. 4, 1987

Related U.S. Application Data

[63] Continuation-in-part of Ser. No. 029,293, Mar. 23, 1987, and a continuation-in-part of Ser. No. 334,053, Dec. 23, 1981, abandoned, Ser. No. 029,293, and Ser. No. 334,053, each is a continuation-in-part of Ser. No. 258,484, Apr. 28, 1981, abandoned, which is a continuation-in-part of Ser. No. 201,649, Oct. 28, 1980, abandoned, which is a continuation-in-part of Ser. No. 199,886, Oct. 23, 1980, abandoned.

[30] Foreign Application Priority Data

Oct. 15, 1981 [EP] European Pat. Off. ......... 81108348.4

[51] Int. Cl.$^4$ ..................... A61K 31/40; C07D 209/26
[52] U.S. Cl. ..................................... 514/19; 514/412; 548/492; 548/533
[58] Field of Search ................. 548/492, 533; 514/412, 514/423, 19

[56] References Cited

U.S. PATENT DOCUMENTS 4,350,704 9/1982 Hoefle et al. ................... 546/147 X
4,374,829 2/1983 Harris et al. ......................... 514/21
4,508,729 4/1985 Vincent et al. ..................... 514/419

FOREIGN PATENT DOCUMENTS 0049658 4/1982 European Pat. Off. ............ 548/492

Primary Examiner—David B. Springer
Attorney, Agent, or Firm—Anita W. Magatti; James R. Nelson; Stephen I. Miller

[57] ABSTRACT

The present invention relates to carboxyalkyl dipeptides which are inhibitors of angiotensin-converting enzyme and are useful as antihypertensive agents and in the treatment of congestive heart failure.

The compounds of the present invention are compounds of the formulae

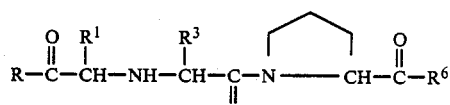

and

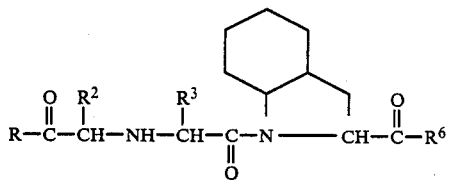

and the pharmaceutically acceptable salts thereof, wherein R and $R^6$ are the same or different and are hydroxy or lower alkoxy;

$R^1$ is benzyloxylower alkyl or benzylthiolower alkyl;

$R^2$ is benzylthiomethyl, 2-phyenylethylthiomethyl, napthylmethylthiomethyl, methylbenzylthiomethyl, 2-(carboxyphenyl)ethyl or 2-(alkoxycarbonylphenyl)ethyl) and $R^3$ is hydrogen, lower alkyl or aminolower alkyl.

21 Claims, No Drawings

CARBOXYALKYL DIPEPTIDES AND MEDICAL USE THEREOF IN TREATING HYPERTENSION AND CONGESTIVE HEART FAILURE

This application is a continuation-in-part of Ser. No. 029,293, filed Mar. 23, 1987 and of Ser. No. 334,053 filed Dec. 23, 1981, now abandoned, both of which are continuations-in-part of Ser. No. 258,484, filed Apr. 28, 1981, now abandoned, which is a continuation-in-part of Ser. No. 201,649, filed Oct. 28, 1980, now abandoned, which is a continuation-in-part of Ser. No. 199,886, filed Oct. 23, 1980, now abandoned.

The present invention relates to carboxyalkyl dipeptides which are inhibitors of angiotensin-converting enzyme and are useful as antihypertensive agents and in the treatment of congestive heart failure.

The compounds of the present invention are compounds of the formulae

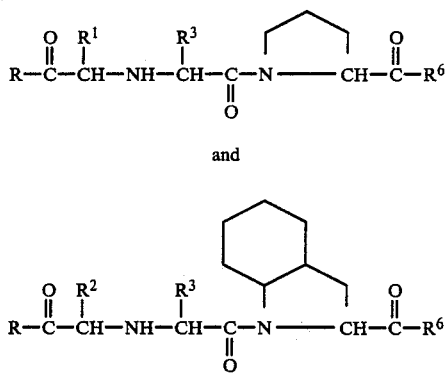

and the pharmaceutically acceptable salts thereof, wherein

R and $R^6$ are the same or different and are hydroxy or lower alkoxy;

$R^1$ is benzyloxylower alkyl or benzylthiolower alkyl;

$R^2$ is benzylthiomethyl, 2-phenylethylthiomethyl, naphthylmethylthiomethyl, methylbenzylthiomethyl, 2-(carboxyphenyl)ethyl or 2-(alkoxycarbonylphenyl)ethyl; and $R^3$ is hydrogen, lower alkyl or aminolower alkyl.

The aforementioned compounds of formulae I and II, as defined above, include all possible stereoisomers. The term "lower alkyl" refers to straight and branched hydrocarbon chains of from one to six carbon atoms, for example, methyl, ethyl, propyl, isopropyl, butyl, isobutyl, t-butyl, pentyl or hexyl. "Alkoxy" similarly refers to alkoxy groups of 1 to 6 carbon atoms.

Preferred compounds of formula I and II are those wherein $R^3$ is lower alkyl, with methyl being more preferred. Also preferred are compounds of formulae I and II wherein $R^6$ is hydroxy. Another group of preferred compounds of formulae I and II are those wherein R is lower alkoxy with ethoxy being more preferred.

Preferred compounds of formula I are those wherein the lower alkyl portion of $R^1$ is methyl.

Preferred compounds of formula II wherein $R^2$ is 2-(alkoxycarbonylphenyl)ethyl are those wherein the alkoxy portion is ethoxy. Where compounds of formula II comprise $R^2$ groups having a substituted phenyl portion, preferred are compounds wherein the substituent on the phenyl ring is in the para position, i.e., wherein $R^2$ is p-methylbenzylthiomethyl, p-carboxyphenylethyl or p-(ethoxycarbonyl)phenylethyl.

Preferred compounds of the present invention are:
N-(1(R)-ethoxycarbonyl-2-benzylthioethyl)-(R,S)-alanyl-(S)-proline,
N-(1(S)-ethoxycarbonyl-2-benzyloxyethyl)-(R,S)-alanyl-(S)-proline,
1-[N-[1(R)-ethoxycarbonyl-2-(benzylthio)ethyl]-(S)-alanyl]-cis,syn-perhydroindole-2(S)-carboxylic acid, and the corresponding (R;R,S;S) isomer thereof,
1-[N-[1(R)-ethoxycarbonyl-2-(2-phenylethylthio)ethyl]-(S)-alanyl]-cis,syn-perhydroindole-2(S)-carboxylic acid,
1-[N-[1(R)-ethoxycarbonyl-2-(2-naphthylmethylthio)ethyl]-(S)-alanyl]-cis,syn-perhydroindole-2(S)-carboxylic acid,
1-[N-[(1(R)-ethoxycarbonyl-2-(4-methylbenzylthio)ethyl]-(R,S)-alanyl]-cis,syn-perhydroindole-2(S)-carboxylic acid,
1-[N-[1(S)-ethoxycarbonyl-3-(4-ethoxycarbonylphenyl)propyl]-(S)-alanyl]-cis,syn-perhydroindole-2(S)-carboxylic acid,
1-[N-[1(S)-carboxy-3-(4-carboxyphenyl)propyl]-(S)-alanyl]-cis,syn-perhydroindole-2(S)-carboxylic acid, and the hydrochloride salts thereof.

The compounds of the present invention can be produced by several methods, two of which are depicted in the following equations. Reactive groups not involved in the condensations described below such as amino, carboxy, mercapto, etc., may be protected by methods standard in peptide chemistry prior to the coupling reactions and subsequently deprotected to obtain the desired products. Such reactions are demonstrated in the Examples.

Method 1, Route 1

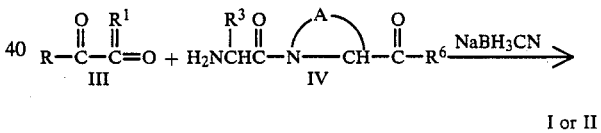

I or II wherein R, $R^1$, $R^3$ and $R^6$ are as defined above and

completes a proline or perhydroindole ring.

Keto acid (or ester) III is condensed with dipeptide IV in aqueous solution, optimally near neutrality, or in a suitable organic solvent (for example, $CH_3OH$) in the presence of sodium cyanoborohydride to give I or II. Alternatively, the intermediate Schiff base, enamine, or aminol may be catalytically reduced to yield product I or II, for example, by hydrogen in the presence of 10% palladium on carbon or of Raney nickel. The ratio of diasteriomeric products formed may be altered by choice of catalyst.

Alternatively III can be condensed with an amino acid V.

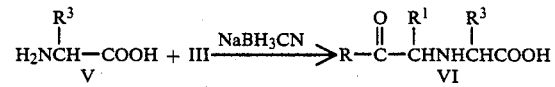

under the same conditions to yield amino acid VI. Subsequent coupling by known methods with amino acid derivative VII gives I or II.

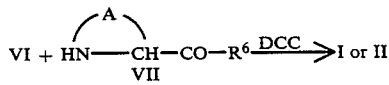

The known methods encompass reactive group protection during the coupling reaction, for example, by N-formyl, N-t-butoxycarbonyl and N-carbobenzyloxy groups followed by their removal to yield I or II. Furthermore, the R function may include removable ester groups such as benzyl, ethyl or t-butyl. Condensing agents in this synthetic route are typically those useful in peptide chemistry such as dicyclohexylcarbodiimide (DCC) or diphenylphosphoryl azide (DPPA) or VI may be activated via the intermediacy of active esters such as that derived from 1-hydroxybenzotriazole (HOBT).

Route 2

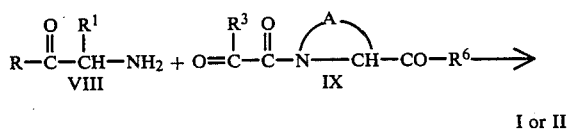

Amino acid (or ester) VIII is condensed with ketone IX under conditions described for Route 1 to give I or II Method II, Route 1

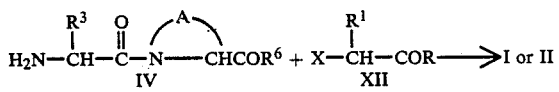

The dipeptide IV is alkylated with the appropriate alpha-haloacid (or ester) or alpha-sulfonyloxy acid (or ester) XII, wherein X is chlorine, bromine, iodine, alkanesulfonyloxy or arenesulfonyloxy, under basic conditions in water or in an organic solvent.

Alternatively, the synthesis can be performed in a step-wise fashion.

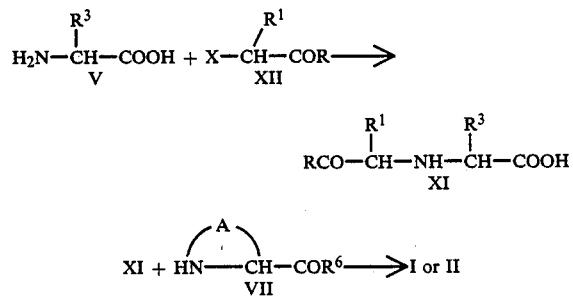

In this stepwise synthesis, X in the compound of formula XII is chlorine, bromine, iodine, alkanesulfonyloxy or arenesulfonyloxy.

The aminoacid V (or a protected ester form thereof, such as t-butyl or benzyl ester) is alkylated by the alpha-haloacid (or ester) or alpha-sulfonyloxy acid (or ester) XII under basic conditions to yield (following ester deprotection, if necessary) compounds XI. This is condensed by standard methods as indicated under Route 1 with the aminoacid (ester or amide) VII to afford I or II.

The starting materials which are required for the above processes herein described are known in the literature or can be made by known methods from known starting materials.

In the compounds of formulae I and II, the carbon atoms to which $R^1$ and $COR^6$ are attached may be asymmetric. The compounds accordingly exist in diastereoisomeric forms or in mixtures thereof. The above described syntheses can utilize racemates, enantiomers or diastereomers as starting materials. Enantiomeric intermediates may be obtained by resolution methods known in the art. When diastereomeric products result from the synthetic procedures, the diastereomeric products can be separated by conventional chromatographic or fractional crystallization methods.

In general, the aminoacid part-structures, i.e.,

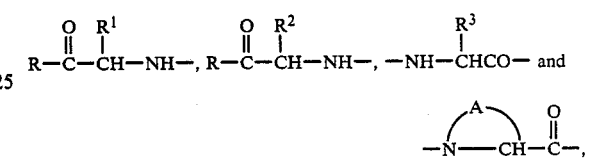

wherein R, $R^1$, $R^2$, $R^3$ and $$\overset{A}{\frown}$$

are as defined above, are preferred in the configuration most similar to that of natural L-amino acids. Usually, natural L-amino acids are assigned to the S-configuration. A notable exception is the natural amino acid L-cysteine which is assigned to the R-configuration.

The compounds of this invention form salts with various inorganic and organic acids and bases which are also within the scope of the invention. Such salts include ammonium salts, alkali metal salts like sodium and potassium salts (which are preferred), alkaline earth metal salts like the calcium and magnesium salts, salts with organic bases e.g., dicyclohexylamine salts, N-methyl-D-glucamine, salts with amino acids like arginine, lysine and the like. Also, salts with organic and inorganic acids may be prepared, e.g., HCl, HBr, $H_2SO_4$, $H_3PO_4$, methanesulfonic acid, toluenesulfonic acid, maleic acid, fumaric acid and camphorsulfonic acid. The nontoxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The following examples illustrate the preparation of the compounds of the present invention. The diastereomers prepared as set forth below may be isolated by column chromatography or by fractional crystallization.

EXAMPLE 1

N-(1(R)-Ethoxycarbonyl-2-benzylthioethyl)-(R,S)-alanyl-(S)-proline hydrochloride Mix S-benzyl-L-cysteine ethyl ester hydrochloride (8.28 g) with NaHCO$_3$ solution until basic. Extract with dichloromethane, dry with MgSO$_4$, and concentrate to dryness at room temperature. Dissolve the residue in tetrahydrofuran (80 ml) containing pyruvoyl-L-proline (2.1 g) and 5 Angstrom molecular sieves (4 g). Stir for 2 days and then add, dropwise over 4 hours, a solution of sodium cyanoborohydride in ethanol (20 ml). Stir for 18 hours, filter, and concentrate the filtrate to dryness. Partition the residue between water and dichloromethane. Absorb the aqueous phase on a sulfonic acid ion exchange resin and elute with 4% pyridine in water. Concentrate to dryness. Dissolve the residue in a miture of methanol (5 ml) and ether (1500 ml). Acidify this solution with 3.5M HCl in ether and filter the resulting precipitate to obtain the title compound (2.5 g), m.p. 90°–100° C. and $[\alpha]^{26}{}_D = -73.4°$ (1%. H$_2$O).

EXAMPLE 2

N-(1(S)-Ethoxycarbonyl-2-benzyloxyethyl)-(R,S)-alanyl-(S)-proline hydrochloride Following the procedure of Example 1, react O-benzyl-L-serine ethyl ester hydrochloride (5 g) with pyruvoyl-L-proline (1.26 g) to yield the title compound (1.6 g, m.p. 90°–100° and $[\alpha]^{26}{}_D = -71.3°$ (1%, H$_2$O).

EXAMPLE 3

1-[N-[1(R)-Ethoxycarbonyl-2-(4-methylbenzylthio)ethyl]-(R,S)-alanyl]-cis,syn-perhydroindole-2(S)-carboxylic acid Following the procedure of Example 1, substitute S-4-methylbenzyl-L-cysteine ethyl ester for S-benzyl-L-cysteine ethyl ester and substitute N-pyruvoyl-(S)-perhydroindole for N-pyruvoyl-L-proline to obtain the title compound, m.p. 55°–60° C.

EXAMPLE 4

1-[N-[1(S)-Ethoxycarbonyl-3-(4-ethoxycarbonylphenyl)propyl]-(S)-alanyl]-cis,syn-perhydroindole-2(S)-carboxylic acid Step 1. 2-Bromo-4-(4-carboxyphenyl)butyric acid: Heat ethyl 2-bromo-4-(4-cyanophenyl)butyrate (16.5 g) in 47–49% hydrobromic acid (160 ml) under reflux for 16 hr. Cool the reaction mixture and dilute with ice to give the title compound, a light tan solid (15.07 g), m.p. 172°–176°.

Step 2. Ethyl 2-bromo-4-(4-ethoxycarbonylphenyl)butyrate: Combine the product of Step 1 (15.07 g), 1,3-dicyclohexylcarbodiimide (22.0 g) and 4-dimethylaminopyridine (1.28 g) in dichloromethane (CH$_2$Cl$_2$) (150 ml) and treat with absolute ethanol (20 ml) at 0°–5° C. and stir for 18 hr. Filter the reaction mixture and concentrate the filtrate in vacuo. Place the residue on a column of silica gel (3L) and elute with hexane:EtOAc 9:1 to give the title compound, a yellow oil (16.90 g).

Step 3. N-[1(R)- and 1(S)-Ethoxycarbonyl-3-(4-ethoxycarbonylphenyl)propyl]-(S)-alanine t-butyl esters: Heat the product of Step 2 (16.90 g) and (S)-alanine t-butyl ester hydrochloride (8.05 g) in dimethylformamide (DMF) (80 ml) and triethylamine (40 ml) at 70° for 20 hr. Concentrate the reaction mixture in vacuo and partition the residue between ethyl acetate (EtOAc) and H$_2$O. Dry (MgSO$_4$) the EtOAc and concentrate in vacuo to give an amber oil (15.86 g). Chromatograph the mixture (8.0 g) on Waters Prep 500 (2 cartridges) using hexane:ethyl acetate 19:1 and 9:1 to give N-[1(R)-ethoxycarbonyl-3-(4-ethoxycarbonylphenyl)propyl]-(S)-alanine t-butyl ester, a pale yellow oil (1.08 g), $[\alpha]^{26}{}_D = -21.6°$ (MeOH) and N-[1(S)-ethoxycarbonyl-3-(4ethoxycarbonylphenyl)propyl]-(S)-alanine t-butyl ester, a pale yellow oil (1.42 g), $[\alpha]^{26}{}_D = -4.6°$ (MeOH) and overlaps (0.1 g).

Step 4. N-[1(S)-Ethoxycarbonyl-3-(4-ethoxycarbonylphenyl)propyl]-(S)alanine: Treat N-[1(S)-ethoxycarbonyl-3-(4-ethoxycarbonylphenyl)propyl]-(S)-alanine t-butyl ester (2.81 g) in CH$_2$Cl$_2$ (40 ml) at 0°–5° with trifluoroacetic acid (TFA) (30 ml). Stir the resulting mixture at 0°–5° for 0.5 hr., warm to room temperature and stir for 6 hr. Concentrate the reaction mixture in vacuo and chromatograph the residue on a column of silica gel (2L), eluting with CHCl$_3$:i-PrOH:7% NH$_4$OH (1:1:1, organic phase) to give the title compound, a white solid (2.06 g), m.p. 145°–147°, $[\alpha]^{26}{}_D = -33.7°$ (MeOH).

Step 5. 1-[N-[1(S)-Ethoxycarbonyl-3-(4-ethoxycarbonylphenyl)propyl-(S)-alanyl]-cis,syn-perhydroindole-2(S)-carboxylic acid t-butyl ester: Add cis,syn-perhydroindole-2(S)-carboxylic acid t-butyl ester (1.28 g) in DMF (10 ml) to the product of Step 4 (2.00 g), DEC (1.10 g) and HOBT (0.90 g). Add N-methylmorpholine (0.63 ml) and stir the resulting mixture at room temperature for 20 hr. Concentrate the reaction mixture in vacuo and partition between EtOAc and H$_2$O. Dry (MgSO$_4$) the EtOAc and concentrate in vacuo to give a pale amber residue. Chromatograph this residue on a column of silica gel (2L), eluting with EtOAc:hexane 1:1 to give the title compound, a colorless oil (2.48 g), $[\alpha]^{26}{}_D = -52.4°$ (MeOH).

Step 6. 1-[N-[1(S)-Ethoxycarbonyl-3-(4-ethoxycarbonylphenyl)propyl]-(S)-alanyl]-cis,syn-perhydroindole-2(S)-carboxylic acid: Treat the product of Step 5 (2.40 g) in CH$_2$Cl$_2$ (40 ml) at 0°–5° with TFA (25 ml). Stir for 0.5 hr., warm to room temperature and stir for 6 hr. Concentrate the reaction mixture in vacuo and chromatograph the residue on a column of silica gel (2L), eluting with CHCl$_3$:i-PrOH:7% NH$_4$OH (1:1:1, organic phase) to give the title compound, a white foam (2.09 g), $[\alpha]^{26}{}_D = -24.4°$ (MeOH).

EXAMPLE 5

1-[N-[1(S)-Carboxy-3-(4-carboxyphenyl)propyl]-(S)-alanyl]-cis,syn-perhydroindole-2(S)-carboxylic acid.

Treat the product of Example 5 (1.01 g) in MeOH (40 ml) at 0°–5° with 1N NaOH (6.0 ml) for 2 hr. Warm the mixture to room temperature and stir for 18 hr. Concentrate the mixture under nitrogen to approximately 10 ml and dilute with H$_2$O (10 ml). Stir for 4 hr., cool the reaction mixture to 0°–5° and treat with 1N HCl to give the title compound, a white solid (0.81 g), $[\alpha]^{26}{}_D = -35.6°$ (MeOH:1N NaOH 3:1).

EXAMPLE 6

1-[N-[1(R)-Ethoxycarbonyl-2-(benzylthio)ethyl]-(S)-alanyl]-cis,syn-perhydroindole-2(S)-carboxylic acid, hydrobromide Step 1. Stir 100 g of S-benzyl-L-cysteine ethyl ester hydrochloride, 132 g of benzyl pyruvate, and 10 g of 3A molecular sieves in 8 liters of ethanol for 18 hours under nitrogen. Add dropwise a solution of 52 g sodium cyanoborohydride in 100 ml of ethanol, stir at room temperature for 24 hours, filter, then concentrate the filtrate at room temperature under vacuum. Suspend the resultant residue in 100 ml water and 500 ml ether and adjust the mixture to pH 8 with 1N HCl. Wash the organic layer with saturated sodium chloride solution, dry over sodium sulfate, and filter. Adjust the filtrate to pH 2 with 3M ethereal HCl, decant the supernatant, wash the resulting oily precipitate with 200 ml ether, and mix with saturated aqueous sodium bicarbonate to obtain a solution of pH 8. Extract the mixture with 1 liter of ether, dry the ether layer over sodium sulfate and concentrate at room temperature to give N-(1(R)-ethoxycarbonyl-2-(benzylthio)ethyl)-(R,S)-alanine benzyl ester, an amber oil. The procedure may be continued on the mixture, or thin layer chromatography in ethyl acetate: hexane (15:85) may be used to separate the two isomers (isomer A at Rf=0.36, and isomer B at Rf=0.28).

Step 2. Add 50 g of the product of Step 1 to 1800 ml of a 15–20% solution of hydrobromic-acetic acid and heat at 50° C. for 20 hours. Concentrate the resultant mixture to dryness under vacuum, and wash the resultant oily residue with ether until free of acetic acid to produce N-(1(R)-ethoxycarbonyl-2-(benzylthio)ethyl)-(R,S)-alanine hydrobromide (or the appropriate isomer), an amber oil.

Step 3. Cool a solution of 50.5 g of the product of Step 2 and 33.4 g cis,syn-perhydroindole-2(S)-carboxylic acid benzyl ester in 1 liter of dimethylformamide to 0° C. under nitrogen, add dropwise a solution of 35.5 g diphenylphosphorylazide in 1 liter of dimethylformamide, followed by a solution of 33.4 g N-methylmorpholine in 200 ml dimethylformamide, also added dropwise, and stir at room temperature for 18 hours. Pour the reaction solution into 3 liters of water, adjust to pH 8 with 1N NaOH, and extract with 4×1 liter ether. Wash the combined ether layers with 1 liter of aqueous sodium chloride, dry the ether layer over magnesium sulfate, filter, and concentrate under vacuum to an amber oil.

Chromatograph the resultant oil on 2 kg silica gel (60–200 mesh) using ether:hexane (90:10). Collect components having Rf 0.38 and Rf 0.61 as indicated by thin layer chromatography on silica gel eluted with ether. The isomer with Rf 0.61 is 1-[N-[1(R)-ethoxycarbonyl-2-(benzylthio)ethyl]-(S)-alanyl]-cis,syn-perhydroindole-2(S)-carboxylic acid benzyl ester.

Step 4. Stir 0.70 g of the (S)-alanyl product of Step 3 and 25 ml of a 15–20% solution of hydrobromic-acetic acid under nitrogen for 2 hours, then concentrate to dryness under vacuum at room temperature. Triturate the resultant residue with ether and filter to obtain 1-[N[1(R)-ethoxycarbonyl-2-(benzylthio)ethyl]-(S)-alanyl]-cis,syn-perhydroindole-2(S)-carboxylic acid hydrobromide as a tan solid, m.p. 124°–125° C.

EXAMPLE 7

1-[N-[1(R)-Ethoxycarbonyl-2-(benzylthio)ethyl]-(R)-alanyl]-cis,syn-perhydroindole-2(S)-carboxylic acid, hydrobromide Prepare the (R)-alanyl compound in a manner similar to that described in Example 6, substituting the fraction corresponding to the (R)-alanyl isomer in Step 3 to obtain the title compound, m.p. 121°–122° C.

EXAMPLE 8

1-[N-[1(R)-Ethoxycarbonyl-2-(benzylthio)ethyl]-(S)-alanyl]-cis,syn-perhydroindole-2(S)-carboxylic acid Step 1. Mix S-benzyl-L-cysteine ethyl ester hydrochloride (13.8 g) with NaHCO$_3$ solution until basic. Extract with dichloromethane, dry with MgSO$_4$, and concentrate to dryness at room temperature. Dissolve the residue in 300 ml of ether containing 5 g of N-pyruvoyloctahydro-1H indole-2(S)-carboxylic acid benzyl ester. Cool to 0° C. and add, dropwise with stirring over 2 hr, a solution of 1.7 g of titanium tetrachloride in 100 ml of hexane. Stir the resultant mixture an additional 18 hr at 25° C. Filter the mixture and evaporate the solvent in vacuo at 25° C. Slurry the residue in 500 ml of ethanol, add sodium cyanoborohydride (1.0 g) and stir under nitrogen for 18 hr. Evaporate the solvent at 25° C. in vacuo, slurry the residue in ethyl acetate (500 ml) and adjust to pH8 with 1N sodium hydroxide. Extract the aqueous layer with ethyl acetate (200 ml), combine the organic layers and dry over anhydrous magnesium sulfate. Evaporate the solvent in vacuo at 25° C. to give an amber oil. This is a diastereomeric mixture. Thin layer chromatography (ether) shows the R—S—S isomer at Rf=0.61 and the R-R-S isomer at Rf=0.38.

Step 2. Chromatograph the resultant oil on 1 Kg silica gel (60–200 mesh) using ether:hexane (90:10). Collect components having Rf 0.38 and Rf 0.61 as indicated by thin layer chromatography on silica gel eluted with ether.

Step 3. Stir 0.70 of the R-S-S product of Step 2 and 25 ml of a 20% solution of hydrobromic-acetic acid under nitrogen for 2 hr, then concentrate to dryness under vacuo at 25° C. Triturate the residue with ether and filter to obtain the R-S-S product hydrobromide salt as a tan solid, m.p. 124°–125° C.

Step 4. Dissolve 0.6 g of the R-S-S product hydrobromide in 50 ml of water:ethanol (90:10) and place this solution on a Dowex-50 ion exchange column (200 g). Elute with water:ethanol (90:10) until the eluent is neutral. Then elute with pyridine:water:ethanol (5:90:5). Concentrate the eluent in vacuo to give the R-S-S product free base, m.p. 52°–56° C., $[\alpha]^{26}_D = -97.0°$ (c=1, methanol).

EXAMPLE 9

1-[N-[1(R)-Ethoxycarbonyl-2-(benzylthio)ethyl]-(R,S)-alanyl]-cis,syn-perhydroindole-2(S)-carboxylic acid, hydrochloride Convert the isomeric mixture of Example 8, Step 1 to the isomeric mixture free base as in Example 8, Step 4. Dissolve 1.0 g of this mixture in 1.0 ml of methanol and dilute to 200 ml with ether. Add a 1.0M solution of hydrogen chloride in ether until a pH of 2. Remove the solvent in vacuo to give the product as a yellow solid, m.p. 124° C.(d), $[\alpha]^{26}_D = -44.7°$ (c=1 methanol).

EXAMPLE 10

1-[N-[1(R)-Ethoxycarbonyl-2-(phenylethylthio)ethyl]-(S) alanyl]-cis,syn-perhydroindole-2(S)-carboxylic acid hydrochloride and 1-[N-[1(R)-Ethoxycarbonyl-2-(phenylethylthio)ethyl]-(R) alanyl]-cis,syn-perhydroindole-2(S)-carboxylic acid hydrochloride Use a procedure similar to Example 8, Step 1, except replace S-benzyl-L-cysteine ethyl ester hydrochloride with S-(2-phenylethyl)-L-cysteine ethyl ester hydrochloride. Silica gel thin layer chromatography (ether) shows the R—S—S isomer at Rf=0.7 and the R—R—S isomer at Rf=0.5. Using the procedures of Example 8, Steps 2 and 3, chromatograph and deprotect. Then in a manner similar to Example 9, convert to the hydrochloride salts: R—S—S isomer, m.p. 178°–180° C.(d), $[\alpha]^{26}_D = -25°$ (c=1 methanol); and R—R—S isomer, m.p. 160° C.(d), $[\alpha]^{26}_D = +13.2°$ (c=1, methanol).

EXAMPLE 11

1-[N-[1(R)-Ethoxycarbonyl-2-(2-naphthylmethylthio)ethyl]-(S)-alanyl]-cis,syn-perhydroindole-2(S)-carboxylic acid hydrochloride and 1-[N-[1(R)-Ethoxycarbonyl-2-(2-naphthylmethylthio)ethyl]-(R) alanyl]-cis,syn-perhydroindole-2(S)-carboxylic acid hydrochloride Use a procedure similar to Example 8, Step 1, except replace S-benzyl-L-cysteine ethyl ester hydrochloride with S-(2-naphthylmethyl)-L-cysteine ethyl ester hydrochloride. Silica gel thin layer chromatography (ether) shows the R—S—S isomer at Rf=0.8 and the R—R—S isomer at Rf=0.6. Using the procedures of Example 8, Steps 2 and 3, chromatograph and deprotect. Then in manner similar to Example 9, convert to the hydrochloride salts: R—S—S isomer, m.p. 110° C(d), $[\alpha]^{26}_D = -39.6°$ (c=1 methanol); and R—R—S isomer, m.p. 180° C.(d), $[\alpha]^{26}_D = +6.5°$ (c=1 methanol).

The compounds of this invention are useful in view of their pharmacological properties. In particular, they possess activity as antihypertensive agents as evidenced by their ability to reduce blood pressure in mammals, including humans, in which the blood pressure has become abnormally elevated, and they may be used in the treatment of congestive heart failure.

The activity of the compounds as inhibitors of angiotensin converting enzyme (ACE) is determined by the following procedure: Sprague-Dawley rats were anesthetized with inactin (100 mg/kg) or dial urethane. Carotid artery and jugular vein were cannulated. Blood pressure was measured from arterial cannula. Drugs were injected intravenously. The animals (2–5) were challenged with angiotensin II (0.3 )g/kg), angiotensin I (0.3 )g/kg) and bradykinin (3 )g/kg) during a control period. The sequence of challenges was repeated 5 min. after iv administration of the test drug. Each animal received at least two doses (increasing by a factor of 10) of test durg. Angiotensin I responses were expressed as a percent of the control response, and an $ID_{50}$ value (concentration at which 50% of the test animals showed a response to angiotensin I) was determined by linear regression analysis.

Following are the results of testing ACE inhibitory activity of several compounds of formulas I and II of this invention (wherein $R^3$ is methyl and $R^6$ is OH) compared to the well-known ACE inhibitors captopril and enalapril.

|  | R | $R^1$ (proline) | $R^2$ (perhydroindole) | Isomer | $ID_{50}$ μg/kg |
|---|---|---|---|---|---|
| 1. | ethoxy | benzylthiomethyl | — | R;R,S;S | 66 |
| 2. | ethoxy | benzyloxymethyl | — | R;R,S;S | 130 |
| 3. | ethoxy | — | benzylthiomethyl | R;R,S;S | 30 |
| 4. | ethoxy | — | benzylthiomethyl | R,S,S | 29 |
| 5. | ethoxy | — | benzylthiomethyl | R,R,S | 350 |
| 6. | ethoxy | — | naphthylmethyl-thiomethyl | R,S,S | >100 |
| 7. | ethoxy | — | naphthylmethyl-thiomethyl | R,R,S | >1,000 |
| 8. | ethoxy | — | phenylethyl-thiomethyl | R,S,S | 32 |
| 9. | ethoxy | — | phenylethyl-thiomethyl | R,R,S | >1,000 |
| 10. | OH | — | 4-carboxy-phenylethyl | S,S,S | 11 |
| 11. | ethoxy | — | 4-methylbenzyl-thiomethyl | R;R,S;S | 88 |
| 12. | captopril |  |  |  | 71 ± 25 |
| 13. | enalapril |  |  |  | 57 ± 7 |
| 14. | enalapril diacid |  |  |  | 15 ± 3 |

The compounds of the present invention can be combined with pharmaceutical carriers and administered in a variety of well known pharmaceutical forms suitable for oral and parenteral administration to provide compositions useful in the treatment of cardiovascular disorders and particularly mammalian hypertension.

The effective dose ($ED_{50}$) of the compounds of this invention will typically be in the range of about 0.01 to about 30 mg/kg, preferably about 0.1 to about 10 mg/kg, of mammalian weight, administered in single or divided doses. The exact dose to be administered is dependent upon where the particular compound lies within the above quoted range, as well as upon the age, weight and condition of the individual.

Generally, in treating humans, the compounds of this invention may be administered to patients in need of such treatment in a dosage range of 5 to 500 mg per patient generally given several times, thus giving a total daily dose of from 5 to 2000 mg per day. Also, the compounds of this invention may be given in combination with diuretics or other antihypertensives. Typically, these are combinations whose individual per day dosages range from one-fifth of the minimally recommended clinical dosages to the maximum recommended levels for the entities when they are given singly. Examples of such diuretics or other antihypertensives are hydrochlorothiazide, chlorothiazide, ethacrynic acid, amiloride, furosemide, propanolol, timolol and methyldopa.

The composition containing the compounds of this invention will preferably contain from about 5 to about 250 mg of the active compound per dosage unit. These compositions are most preferably administered orally. Typical formulations for oral administration are those such as tablets, capsules, syrups, elixirs or suspensions. Typical injectable formulations include solutions and suspensions.

Typical acceptable pharmaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

The following examples describe in detail compositions that are illustrative of the present invention. It will be apparent to those skilled in the art that many modifications, both of materials and methods, may be practiced without departing from the purpose and intent of this disclosure.

In the following examples, the active ingredient is preferably one of the compounds named on page 3.

EXAMPLE 12

| Capsule | Amount (mg) | |
|---|---|---|
| Active ingredient | 250.0 | 125.0 |
| Lactose | 173.0 | 86.5 |
| Corn Starch | 75.0 | 37.5 |
| Magnesium Stearate | 2.0 | 1.0 |
| | 500.0 | 250.0 |

Blend the active ingredient, lactose and corn starch until uniform; then blend the magnesium stearate into the resulting powder. Encapsulate the mixture into suitable sized two-piece hard gelatin capsules.

| Tablet | Amount (mg) | |
|---|---|---|
| Active ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |

-continued

| Tablet | Amount (mg) | |
|---|---|---|
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 14

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°–70° C. and cool the solution to 25°–35° C. Charge and dissolve all other excipients and the active ingredient. Bring the solution to final volume, filter it through a sterilizing membrane and fill into sterile containers.

We claim:

1. A compound represented by the formula

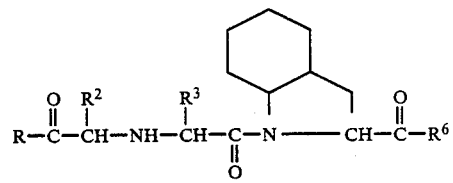

and the pharmaceutically acceptable salts thereof, wherein

R and $R^6$ are the same or different and are hydroxy or lower alkoxy;

$R^2$ is benzylthiomethyl, 2-phenylethylthiomethyl, naphthylmethylthiomethyl, methylbenzylthiomethyl, carboxyphenylethyl or alkoxycarbonylphenylethyl; and $R^3$ is hydrogen, lower alkyl or aminolower alkyl.

2. A compound of claim 1 wherein R is lower alkoxy.

3. A compound of claim 1 wherein R is ethoxy.

4. A compound of claim 1 wherein $R^6$ is hydroxy.

5. A compound of claim 1 wherein $R^3$ is lower alkyl.

6. A compound of claim 1 wherein $R^3$ is methyl.

7. A compound of claim 1 wherein $R^2$ is benzylthiomethyl.

8. A compound of claim 1 wherein $R^2$ is 2-phenylethylthiomethyl.

9. A compound of claim 1 wherein $R^2$ is naphthylmethylthiomethyl.

10. A compound of claim 1 wherein $R^2$ is methylbenzylthiomethyl.

11. A compound of claim 1 wherein $R^2$ is carboxyphenylethyl.

12. A compound of claim 1 wherein $R^2$ is alkoxycarbonylphenylethyl.

13. A compound of claim 12 wherein $R^2$ is ethoxycarbonylphenylethyl.

14. A compound of claim 1 wherein R is lower alkoxy, $R^6$ is hydroxy, $R^3$ is lower alkyl, and $R^2$ is benzylthiomethyl, 2-phenylethylthiomethyl, naphthylmethylthiomethyl, methylbenzylthiomethyl, carboxyphenylethyl or ethoxycarbonylphenylethyl.

15. A compound of claim 14 wherein R is ethoxy and $R^3$ is methyl.

16. A compound of claim 14 selected from 1-[N-[1(R)-ethoxycarbonyl-2-(4-methylbenzylthio)ethyl]-(R,S)-alanyl]-cis,syn-perhydroindole-2(S)-carboxylic acid;
1-[N-[1(S)-ethoxycarbonyl-3-(4-ethoxycarbonylphenyl)propyl]-(S)-alanyl]-cis,syn-perhydroindole-2(S)carboxylic acid;
1-[N-[1(R)-ethoxycarbonyl-2-(benzylthio)ethyl]-(R,S)-alanyl]-cis,syn-perhydroindole-2(S)-carboxylic acid;
1-[N-[1(R)-ethoxycarbonyl-2-(phenylthio)ethyl]-(S)-alanyl]-cis,syn-perhydroindole-2(S)-carboxylic acid;
1-[N-[1(R)-ethoxycarbonyl-2-(2-naphthylmethylthio)ethyl]-(S)-alanyl]-cis,syn-perhydroindole-2(S)-carboxylic acid.

17. A compound of claim 11 wherein R is hydroxy and $R^3$ is methyl.

18. A compound of claim 17 which is 1-[N-(1(S)-carboxy-3-(4-carboxyphenyl)propyl]-(S)-alanyl]-cis,syn-perhydroindole-2(S)-carboxylic acid.

19. An antihypertensive pharmaceutical composition comprising an antihypertensive effective amount of a compound of claim 1, together with a pharmaceutically acceptable carrier.

20. A method for reducing blood pressure in a hypertensive mammal which comprises administering to such a mammal a composition of claim 19.

21. A method of treating congestive heart failure in a mammal in need of such treatment comprising administering to such a mammal an amount of a compound of claim 1 effective in treating congestive heart failure.

* * * * *

UNITED STATES PATENT AND TRADEMARK OFFICE
CERTIFICATE OF CORRECTION

PATENT NO. : 4,818,749
DATED : April 4, 1989
INVENTOR(S) : Elijah H. Gold et al.

It is certified that error appears in the above-identified patent and that said Letters Patent is hereby corrected as shown below:

In column 14, line 2, after "acid;" insert -- 1-[N-[1(R)-ethoxycarbonyl-2-(benzylthio)ethyl]-(S)-alanyl]-cis,syn-perhydroindole-2(S)-carboxylic acid;--.

Signed and Sealed this

Thirteenth Day of March, 1990

*Attest:*

JEFFREY M. SAMUELS

*Attesting Officer*     *Acting Commissioner of Patents and Trademarks*